United States Patent
Uno

(10) Patent No.: US 9,547,888 B2
(45) Date of Patent: Jan. 17, 2017

(54) ULTRASONIC DIAGNOSTIC APPARATUS

(71) Applicant: HITACHI ALOKA MEDICAL, LTD., Mitaka-shi, Tokyo (JP)

(72) Inventor: Takaya Uno, Mitaka (JP)

(73) Assignee: Hitachi, Ltd., Tokyo (JP)

( * ) Notice: Subject to any disclaimer, the term of this patent is extended or adjusted under 35 U.S.C. 154(b) by 191 days.

(21) Appl. No.: 14/375,701

(22) PCT Filed: Nov. 8, 2012

(86) PCT No.: PCT/JP2012/079014
§ 371 (c)(1),
(2) Date: Jul. 30, 2014

(87) PCT Pub. No.: WO2013/118359
PCT Pub. Date: Aug. 15, 2013

(65) Prior Publication Data
US 2015/0080728 A1    Mar. 19, 2015

(30) Foreign Application Priority Data

Feb. 6, 2012 (JP) .................................. 2012-022887

(51) Int. Cl.
*A61B 8/00* (2006.01)
*G06T 3/40* (2006.01)
(Continued)

(52) U.S. Cl.
CPC .......... *G06T 3/4092* (2013.01); *G01S 7/52033* (2013.01); *G06T 3/4007* (2013.01);
(Continued)

(58) Field of Classification Search
CPC .. G06T 3/4092; G06T 3/4007; G06T 2210/36; G06T 2210/41; G06T 2200/16; G01S 7/52033; A61B 8/5207
(Continued)

(56) References Cited

U.S. PATENT DOCUMENTS 6,413,217 B1 * 7/2002 Mo ...................... G01S 7/52034
600/440
2002/0015101 A1 * 2/2002 Mead ................... H04N 3/1562
348/333.01
(Continued)

FOREIGN PATENT DOCUMENTS

CN    101249002 A    8/2008
JP    64-86947 A    3/1989
(Continued)

OTHER PUBLICATIONS

Notification of Transmittal of Copies of Translation of the International Preliminary Report on Patentability (Chapter I or Chapter II) PCT/IB/338 of International Application No. PCT/JP2012/079014 mailed Aug. 14, 2014 with PCT/IPEA/409.
(Continued)

*Primary Examiner* — Sanjay Cattungal
(74) *Attorney, Agent, or Firm* — Westerman, Hattori, Daniels & Adrian, LLP

(57) ABSTRACT

In an ultrasonic diagnostic apparatus, a scan converter module generates display frame data from received frame data using a conversation table adapted to the specific display resolution of a display device. Received frame data is stored in a first frame memory, and display frame data is stored in a second frame memory. A control unit selects the conversion table corresponding to the specific display resolution of the display device from among a group of conversion tables. An address converter generates an address set corresponding to a display address using the selected conversion table. Interpolation is then performed based on the echo data specified by this.

8 Claims, 6 Drawing Sheets

(51) Int. Cl.
*G01S 7/52* (2006.01)
*A61B 8/08* (2006.01)

(52) U.S. Cl.
CPC ......... *A61B 8/5207* (2013.01); *G06T 2200/16* (2013.01); *G06T 2210/36* (2013.01); *G06T 2210/41* (2013.01)

(58) Field of Classification Search
USPC ..................... 600/437–469; 382/128–132
See application file for complete search history.

(56) References Cited

U.S. PATENT DOCUMENTS

| | | | | |
|---|---|---|---|---|
| 2008/0205715 | A1* | 8/2008 | Halmann | ................ A61B 8/00 382/128 |
| 2008/0208061 | A1* | 8/2008 | Halmann | ................ A61B 8/13 600/459 |
| 2012/0057767 | A1 | 3/2012 | Halmann | |

FOREIGN PATENT DOCUMENTS

| | | |
|---|---|---|
| JP | 2000-79122 A | 3/2000 |
| JP | 2000-139910 A | 5/2000 |
| JP | 2000-310621 A | 11/2000 |
| JP | 2001-285627 A | 10/2001 |
| JP | 2002-143151 A | 5/2002 |
| JP | 2011-123084 A | 6/2011 |
| JP | 2011-234788 A | 11/2011 |

OTHER PUBLICATIONS

Notice of Grounds for Rejection dated Mar. 12, 2014 issued in corresponding application No. JP2012022887; w/ excerpt English Translation; 6 pages.
International Search Report dated Dec. 4, 2012 issued in correponding application No. PCT/JP2012/079014.
Office Action dated Aug. 5, 2015, issued in counterpart Chinese Application No. 201280069166.8 (5 pages).

\* cited by examiner

ULTRASONIC DIAGNOSTIC APPARATUS

TECHNICAL FIELD

The present invention relates to an ultrasonic diagnostic apparatus, and more particularly to a scan converter module that converts a received frame data sequence to a display frame data sequence.

BACKGROUND ART

Ultrasonic diagnostic apparatuses are apparatuses configured to display an ultrasonic image through transmission and reception of ultrasound to and from a living organism. More specifically, with electronic scanning of ultrasonic beams, received frame data formed of a plurality of beam data items is generated. The individual beam data item is subjected to detection processing, logarithmic transformation, re-sampling (decimation) processing, and other processing. The received frame data (a plurality of beam data items) having been subjected to such processing is converted into display frame data (a plurality of line data items) by a scan converter module. The display frame data is then subjected to display processing by means of a video processor, and the display frame data which has been processed is displayed as an ultrasonic image on a display device. In the ultrasonic diagnostic apparatus disclosed in Patent Document 1, a re-sampler is provided upstream of the scan converter.

PRIOR ART DOCUMENT

Patent Document

Patent Document 1: JP 2000-139910 A

DISCLOSURE OF THE INVENTION

Technical Problems

While CRTs were conventionally used as a display device provided in ultrasonic diagnostic apparatuses, they have been recently replaced with flat panel displays such as liquid crystal display devices. These display devices include pixels in the vertical and horizontal directions in numbers that are physically determined, and therefore have a specific display resolution, such as 1024×768 pixels (Extended Graphics Array), 1280×1024 pixels (Super-XGA), and 1600×1200 pixels (Ultra-XGA). Each display device includes therein an adjusting circuit for making input display frame data conform to the display resolution specific to the display device. Specifically, if the resolution of the input display frame data does not correspond to the display resolution specific to the display device, the adjusting circuit provided in the display device executes processing for making the resolution of the input display frame data conform to the display resolution specific to the display device. More accurately, the adjusting processing refers to processing for making the numbers of pixels in the horizontal and vertical directions correspond to the numbers of pixels in the horizontal and vertical directions specific to the display device.

In conventional ultrasonic diagnostic apparatuses, re-sampling processing for making the resolutions of individual beam data correspond to a predetermined resolution is executed before the scan converting processing. The scan converter receives input of a data sequence having been subjected to such re-sampling processing and generates display frame data having a predetermined resolution irrespective of a display device which is connected. When a display device having a higher resolution than that of the apparatus body is connected to the apparatus, for example, the resolution of the display frame data is converted to a higher resolution in a post-event manner at a subsequent stage of the scan converter. This structure, however, raises a problem that the image quality of an ultrasonic image is degraded. Here, if the display frame data is generated with the resolution thereof being adjusted to the highest display resolution, ex-post decimation and other processing must be executed in cases of a certain specific display resolution of a display device, which leads to a problem that efficiency of the scan converting processing is reduced and also the decimation processing affects the image quality.

Similarly, when zoom processing, in which the number of pixels is increased in a post event manner, is executed with respect to the display frame data, a problem of the image quality deterioration arises as in the above case.

The present invention is aimed at realizing scan converting processing which can result in improvement in quality of an ultrasonic image, or at realizing adaptive scan converting processing adapted to various conditions such as a display resolution of a display device. Alternatively, the present invention is aimed at enabling construction of display frame data with the maximum use of obtained information.

Solution to Problems

The ultrasonic diagnostic apparatus according to the present invention is characterized by including a scan converter module that executes conversion processing of converting received frame data obtained by transmitting and receiving ultrasound into display frame data; a display device that displays the display frame data as an ultrasonic image; and a control unit that controls the conversion processing executed by the scan converter module based on a specific display resolution of the display device.

With the above structure, in the scan converter module, adaptive conversion processing (scan converting processing) in accordance with a specific display resolution (the number of vertical and horizontal pixels, in general) of the display device is executed. Preferably, display frame data having the number of pixels conforming to the specific display resolution is generated. If a display device is replaced and therefore the specific display resolution is changed, the content of the conversion processing is also changed accordingly. As this structure basically eliminates the need to adjust the number of pixels after the scan converting processing, the problem of deterioration of the image quality caused by ex-post addition of the number of pixels can be solved, and the problem of a reduction in the conversion efficiency caused by ex-post reduction (decimation) of the number of pixels can also be solved.

It is preferable that the scan converter module is substantially implemented as a function of software except for a portion corresponding to a storage device. In this case, the function may be implemented by a dedicated processor or by a main processor. When the scan converter module is constructed by software, it is possible to cause the scan converter module to execute the same program a plurality of times in parallel, to thereby apparently execute a plurality of scan converting processes simultaneously. In this case, it is possible to generate a plurality of different types of display frame data from the same received frame data in real time.

Preferably, beam data output from a receiving beam former is input directly to the scan converter module without being subjected to re-sampling processing, which is decimation processing. With such full data transfer, it is possible to make use of more information obtained from within a living organism for forming an image, so that the image quality of the ultrasonic image can be enhanced.

Preferably, the control unit controls the conversion processing in the scan converter module based on the specific display resolution of the display device and the display magnification of the ultrasonic image. Information indicating the specific display resolution may be automatically obtained from the display device itself. In this case, EDID (Extended Display Identification Data) which specifies the specific display resolution may be obtained from the display device. Alternatively, the specific display resolution may be registered by the user. By considering the display magnification as well, it is possible to execute, during the scan converting processing, zoom processing (enlargement and reduction of an image) simultaneously, so that the problems of deterioration of the image quality and reduction in the efficiency caused by ex-post adjustment performed after the scan conversion can be avoided. The scan converter module may further execute image segmentation.

Preferably, the scan converter module includes an address generating unit that sequentially generates a display address in accordance with the specific display resolution; an address conversion unit that generates an address set from the display addresses by using an address conversion table created in accordance with the specific display resolution and the display magnification; an interpolation unit that extracts a data set designated by the address set from the received frame data and generates interpolation data according to an interpolation operation by using the data set; and a memory configured to construct the display frame data and store the interpolation data at a memory address corresponding to the display address. With this structure, an address set (a plurality of received point addresses) corresponding to a display address is generated, a plurality of data sections specified by the address set are extracted from the received frame data, and pixel values corresponding to the display address (interpolation data) are generated by using the interpolation operation in which the extracted data is used. When the specific display resolution or the display magnification is changed, the address conversion table conforming to the new specific display resolution or display magnification is selected or generated, and interpolation processing is executed while using the address conversion table. A necessary address conversion calculation may be executed immediately in each case.

Preferably, the control unit obtains information indicating the specific display resolution from the display device. For example, such information is automatically obtained upon connecting the display device to the apparatus body. Alternatively, such information is automatically obtained when powering on the apparatus or connecting a display device cable. The information may be registered manually rather than obtained automatically.

Preferably, the above ultrasonic diagnostic apparatus further includes a receiving beam former that sequentially outputs beam data items forming the received frame data according to phase alignment and summation processing with respect to a plurality of receiving signals obtained by transmitting and receiving the ultrasound, and each of the beam data items is formed as an echo data sequence in accordance with a diagnostic range and the echo data sequence output from the receiving beam former is input to the scan converter module without being subjected to re-sampling processing. With this structure, it is possible to transmit all of the obtained data to the scan converter module without being unnecessarily decimated. However, a part of the data may be deleted from a different viewpoint such as limitation to the display area, noise processing, and so on.

Preferably, the scan converter module converts a received frame rate corresponding to a transmitting/receiving frame rate to a predetermined display frame rate. With this structure, frame rate conversion is performed simultaneously with address conversion.

Preferably, the scan converter module executes n conversion processes for generating n types (where n is an integer which is 2 or greater) of display frame data from the received frame data. With this structure, n types of display frame data is generated from the same received frame data by n conversion processes. With the use of a single scan converter module in a multiple manner or in a repeated manner, it is possible to generate a plurality of images to be displayed on the same screen in real time, for example, or to generate a plurality of images to be displayed on a plurality of display devices in real time. In the latter case, preferably, information indicating the specific display resolution is obtained for each display device so that images having resolutions conforming to the individual display devices are generated.

Preferably, the scan converter module generates the n types of display frame data on a storage region within one period of the display frame rate.

BEST MODE FOR CARRYING OUT THE INVENTION

Preferred embodiments of the present invention will be described with reference to the drawings.

Figure 1:
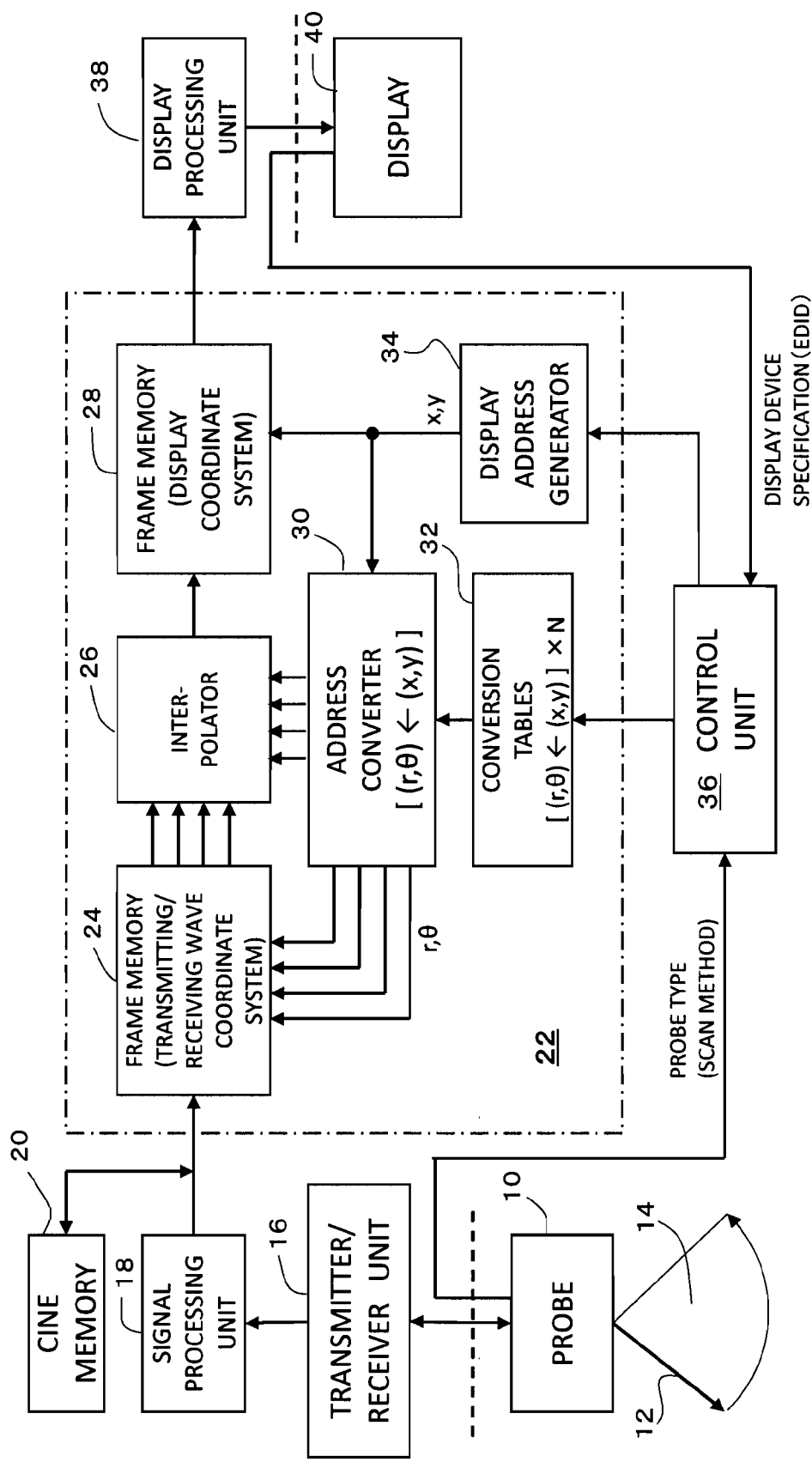
FIG. 1 Block diagram illustrating an ultrasonic diagnostic apparatus according to a preferred embodiment of the present invention.

FIG. 1 illustrates an ultrasonic diagnostic apparatus according to a preferred embodiment of the present invention in a block diagram which illustrates the overall structure of the ultrasonic diagnostic apparatus. This ultrasonic diagnostic apparatus is used in the medical field, and forms an ultrasonic image through transmission and reception of ultrasound to and from a living organism.

Referring to FIG. 1, a probe 10 is a wave transmitter/receiver that performs transmission and reception of ultrasound. The probe 10 is connected to an apparatus body via a probe cable. The probe 10 includes a 1D array transducer which is composed of a plurality of transducer elements arranged in a straight line, for example. An ultrasonic beam 12 is formed by the array transducer as described above, and a beam scanning plane 14, which is a two dimensional echo data capturing region, is formed by electronically scanning the ultrasonic beam 12. It is also possible to provide a 2D array transducer on the probe 10.

A transmitter/receiver unit 16 is formed of a transmitting beam former and a receiving beam former. At the time of transmission, the transmitter/receiver unit 16 supplies a plurality of transmitting signals to the array transducer, thereby forming a transmitting beam. At the time of reception, a reflected wave from within the living organism is received by the array transducer, which generates a plurality of receiving signals which are then output from the array transducer to the transmitter/receiver unit 16. The transmitter/receiver unit 16 executes phase alignment and summation processing with respect to the plurality of receiving signals and outputs the receiving signals (beam data) having been subjected to phase alignment and summation. The beam data is an RF signal and may form a complex signal. In the drawing, a broken line between the probe 10 and the transmitter/receiver 16 indicates a connection section with the apparatus body.

In the present embodiment, a signal processing unit 18 executes signal processing for forming a B-mode image, which includes detection processing, logarithmic transformation, and other processing, with respect to the beam data. In the present embodiment, re-sampling processing is not executed, and all the beam data output from the transmitter/receiver 16 is basically transmitted to a frame memory 24. A cine memory 20 has a structure of a ring buffer and sequentially stores each beam data input in the order of time sequence. After freeze, each beam data read from the cine memory 20 as required is output to the frame memory 24.

In FIG. 1, reference numeral 22 refers to a scan converter module, which is implemented substantially as a function of software except for a portion corresponding to a storage device. In the present embodiment, each of the processes in the downstream stages with respect to the transmitter/receiver unit 16 is implemented by the function of software. Each process may be executed by a processor dedicated to the process or may be executed by a central processor.

As illustrated in FIG. 1, according to the present embodiment, the scan converter module 22 includes a frame memory (first frame memory) 24, an interpolator 26, a frame memory (second frame memory) 28, and so on. The frame memory 24 includes a memory space corresponding to transmitting and receiving wave coordinates, and received frame data is stored in the frame memory 24. One received frame data is composed of a plurality of beam data items, and each beam data item is composed of a plurality of echo data elements arranged in the depth direction. One received frame data corresponds to the beam scan plane 14. On the other hand, the frame memory 28 includes a memory space corresponding to display coordinates, and display framed data is stored on the frame memory 28. As will be described below, interpolation data is generated as a pixel value for each of the individual display addresses (display pixel locations), and the interpolation data is stored at a memory address corresponding to the display address on the frame memory 28. Such processing is executed in a repeated manner for each display address, and one display frame data is finally constructed on the frame memory 28.

In order to perform the interpolation data generation processing described above, the scan converter module 22 includes an address converter 30, a memory 32 storing conversion tables, and a display address generator 34. A specific conversion table designated by a control unit 36 is read from among the conversion tables stored in the memory 32 and is then supplied to the address converter 30 which is formed as a memory and so on. The display address generator 34 functions as a counter which sequentially generates the first to the final numbered display address. Receiving the display address (noted display address) from the display address generator 34, the address converter 30 generates an address set by using the conversion table stored therein and outputs the generated address set to the frame memory 24. It is also possible to calculate and obtain an address set which is necessary in each case.

In the present embodiment, the address set designates real data addresses at four neighboring points about the noted display address. Thus, four echo data sections necessary for the interpolation processing are output from the frame memory 24 to the interpolator 26. The interpolator 26 executes weighted summation processing (interpolation processing) based on these four echo data sections to thereby generate interpolation data. The interpolation data is then stored at a memory address corresponding to the noted display address on the frame memory 28. Here, a weighted data set has been supplied from the address converter 30 to the interpolator 26, which executes the interpolation processing by using the weighted data set. The weighted data set also constitutes the content of the conversion table.

In FIG. 1, as the probe 10 executes electronic sector scan, the display addresses have been converted to the transmitting/receiving wave addresses in accordance with the coordinate system corresponding to the electronic sector scan, accordingly. In FIG. 1, for the purpose of explaining the invention, the display address is specified as x and y and the transmitting/receiving wave address is specified as r and θ.

The conversion tables stored in the memory 32 correspond to the specifications of a plurality of display devices which can be connected with this ultrasonic diagnostic apparatus body. In other words, a plurality of conversion tables are provided corresponding to a plurality of types of display resolutions. As will be described below, the control unit 36, referring to display device specification data (EDID) read from the display device 40, specifies a specific display resolution of the display device 40, and also specifies the scan method in accordance with probe type information read from the probe 10, so as to specify, based on the information thus read, the conversion table to be used in the current situation from among the conversion tables 32. In the present embodiment, the conversion tables corresponding to electronic sector scan are stored in the memory 32. Conversion tables corresponding to electronic linear scan may additionally be stored therein. Alternatively, conversion tables may be provided in accordance with the types of the probe. The control unit 36 supplies information necessary for generating the display address to the display address generator 34. More specifically, the control unit 36 transmits information for specifying the display pixel matrix to the display address generator 34.

A display processing unit 38, which is provided with an image combining function, a color computation function, and so on, applies necessary processing to the input display frame data and transmits the processed data to the display device 40. In the present embodiment, the display device 40 is formed of an electronic display device such as an LCD, and a B-mode image (two dimensional tomographic image) which is based on the display frame data is displayed on a display screen of the display device 40.

In the present embodiment, at the time of starting up the apparatus, at the time of connecting the display device 40, and other necessary times, the display device specification data, i.e. EDID, is read from the storage unit within the display device 40 and the control unit 36 refers to the data thus read. A broken line between the display processing unit 38 and the display device 40 indicates a cable connection section. However, in place of reading such information from the display device 40, a user may manually register the specific display resolution of the display device in the apparatus.

With the structure illustrated in FIG. 1, in which during the scan converting processing, i.e. conversion processing, necessary pixel data can be generated in consideration of the specific display resolution of the display device, i.e. conversion processing adapted to the display device 40 can be performed in the scan converter module 22, it is not necessary to perform addition or decimation of data after the conversion processing, so that an advantage that the image quality can be enhanced and also excessive conversion processing can be prevented can be obtained. As the scan converter module 22 of the present embodiment is also provided with a function of converting the transmitted/received frame rate to the display frame rate, it is not necessary to perform conversion of the frame rate and conversion of the resolution downstream of the scan converter module 22. On the other hand, all the echo data sequences constituting the beam data that are output from the receiving beam former are input to the scan converter module 22, i.e. as the re-sampling processing as conventionally performed is not performed in midstream, an advantage that it is possible to construct display frame data by making the most of the received information obtained from within the living organism can be obtained.

While FIG. 1 illustrates the processing concerning a B-mode image, it is possible to apply the scan conversion processing described above to other types of images such as a two-dimensional blood stream image, a harmonic image, and so on.

Figure 2:
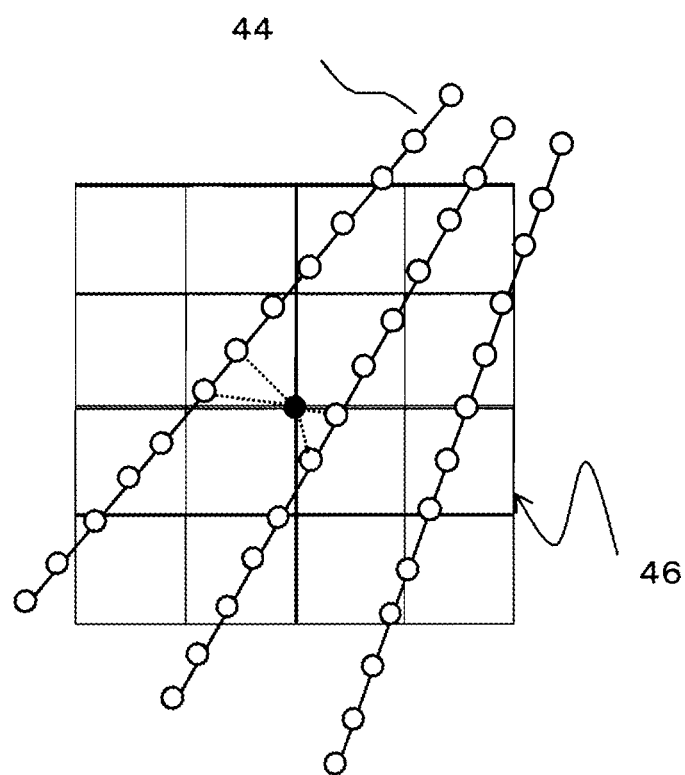
FIG. 2 View illustrating a relationship between a beam data array and a pixel matrix having a low resolution.
Figure 3:
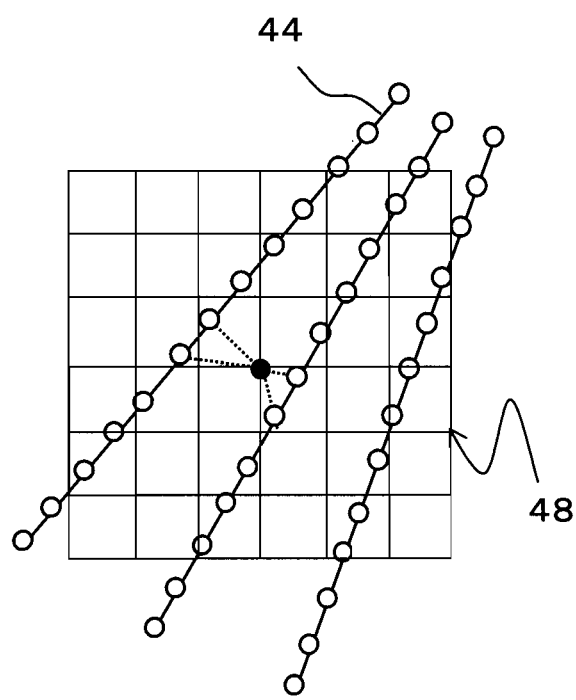
FIG. 3 View illustrating a relationship between a beam data array and a pixel matrix having an intermediate resolution.
Figure 4:
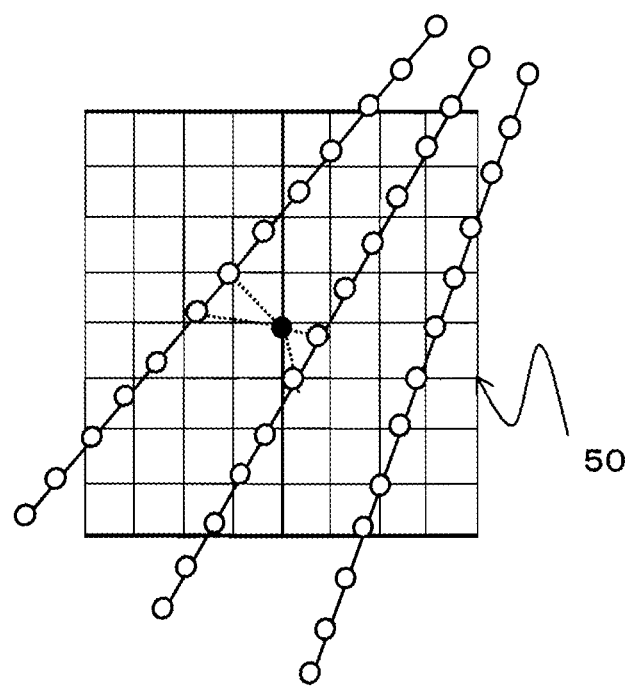
FIG. 4 View illustrating a relationship between a beam data array and a pixel matrix having a high resolution.

With reference to FIGS. 2 to 4, a specific example of the scan converting processing illustrated in FIG. 1 will be described. FIG. 2 illustrates a relationship between the beam data array and a pixel matrix having a low resolution. The beam data array is composed of a plurality of beam data items 44, each of which is composed of a plurality of echo data sections arranged in the depth direction. The pixel matrix 46 is an arrangement of pixels, i.e., a pixel array on the display screen, in which each intersection corresponds to a pixel. In FIG. 2, a white circle represents echo data and a black circle represents a noted pixel on the pixel matrix, which corresponds to the noted display address described above. FIG. 3 illustrates a relationship between the beam data array and a pixel matrix 48 having an intermediate resolution, and FIG. 4 illustrates a relationship between the beam data array and a pixel matrix 50 having a high resolution.

According to the present embodiment, the beam data output from the receiving beam former is directly input to the scan converter module. On the other hand, during the scan converting processing, conversion processing in accordance with the specific display resolution of a display device is executed. While, conventionally, conformation to the display resolution of the display device has been performed in a downstream stage of the scan converting processing, in the present embodiment, processing for conforming to the resolution can be performed simultaneously with the originally-intended scan converting processing.

As has been described with reference to FIG. 1, four echo data items existing in the vicinity of the noted display address are specified, and with weighted summation based on the four specified echo data sections, interpolation data is generated. As the interpolation conditions vary in accordance with the resolution of a display device, the conversion table to be used is switched in accordance with the specific resolution of the display device, as described above.

Figure 5:
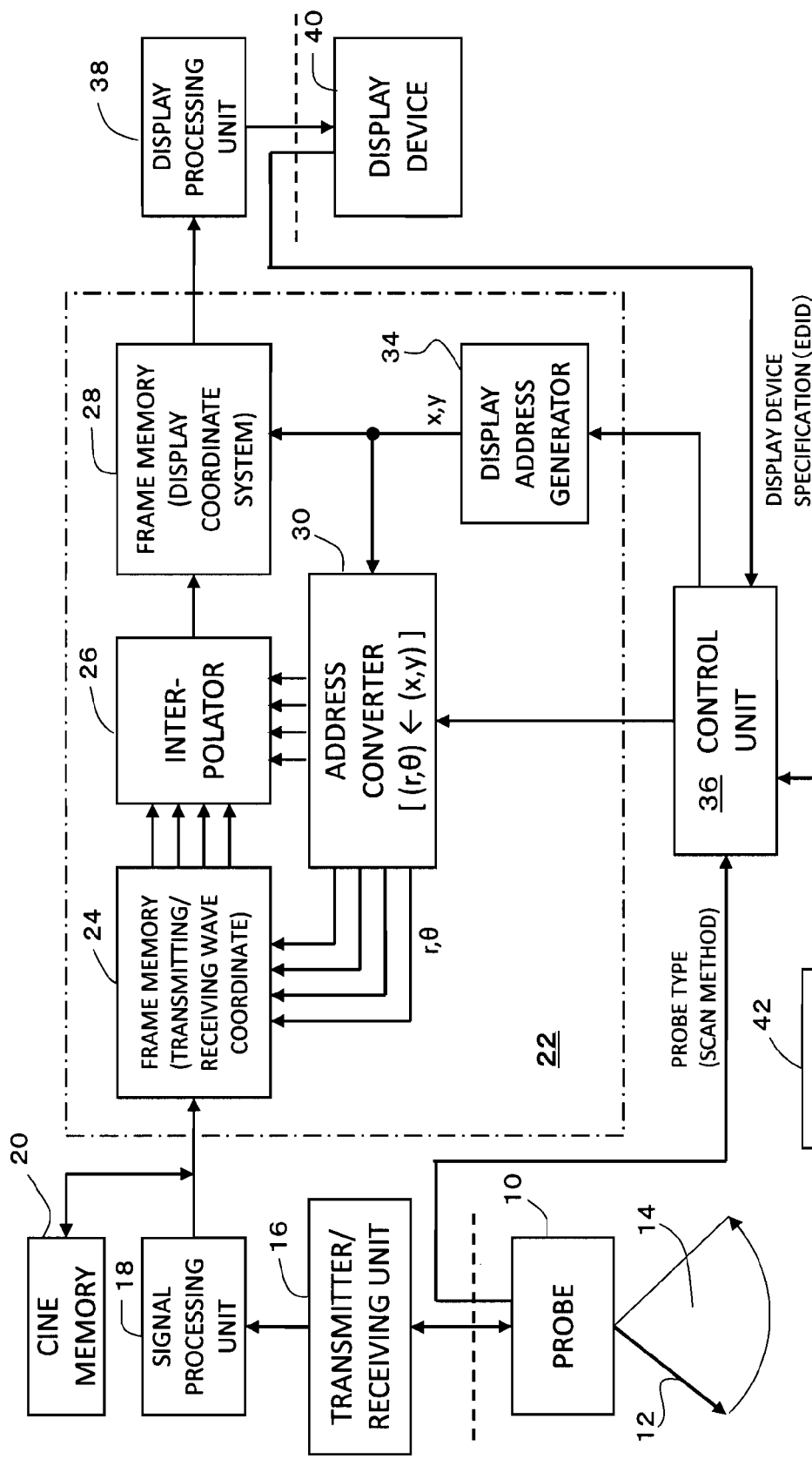
FIG. 5 Block diagram illustrating an ultrasonic diagnostic apparatus according to another embodiment of the present invention.

FIG. 5 illustrates, as a block diagram, a structure of an ultrasonic diagnostic apparatus according to another embodiment. Elements similar to those illustrated in FIG. 1 are denoted by the same reference numerals and description thereof will be omitted.

In the embodiment illustrated in FIG. 5, the control unit 36, in accordance with the probe type, specification of the display device (EDID), and display conditions, calculates and generates a conversion table at a necessary timing, and supplies the conversion table, which is a result of the calculation, to the address converter 30. In this embodiment, the display conditions are identified based on the input to the operation panel 42. The display conditions include a magnification, which is determined by the user based on the zoom designation. When the user sets a region of interest or a display area, information concerning the display size will also be considered.

In accordance with the information described above, in order to allow the display frame data to be output directly to the display device after the scan converting processing, i.e. in order to eliminate the need for changing the data sequence after the scan converting processing, the processing for conforming to the display resolution, and also the zoom processing, are executed simultaneously with the scan converting processing. Segmentation processing with respect to a display portion may also be performed.

Figure 6:
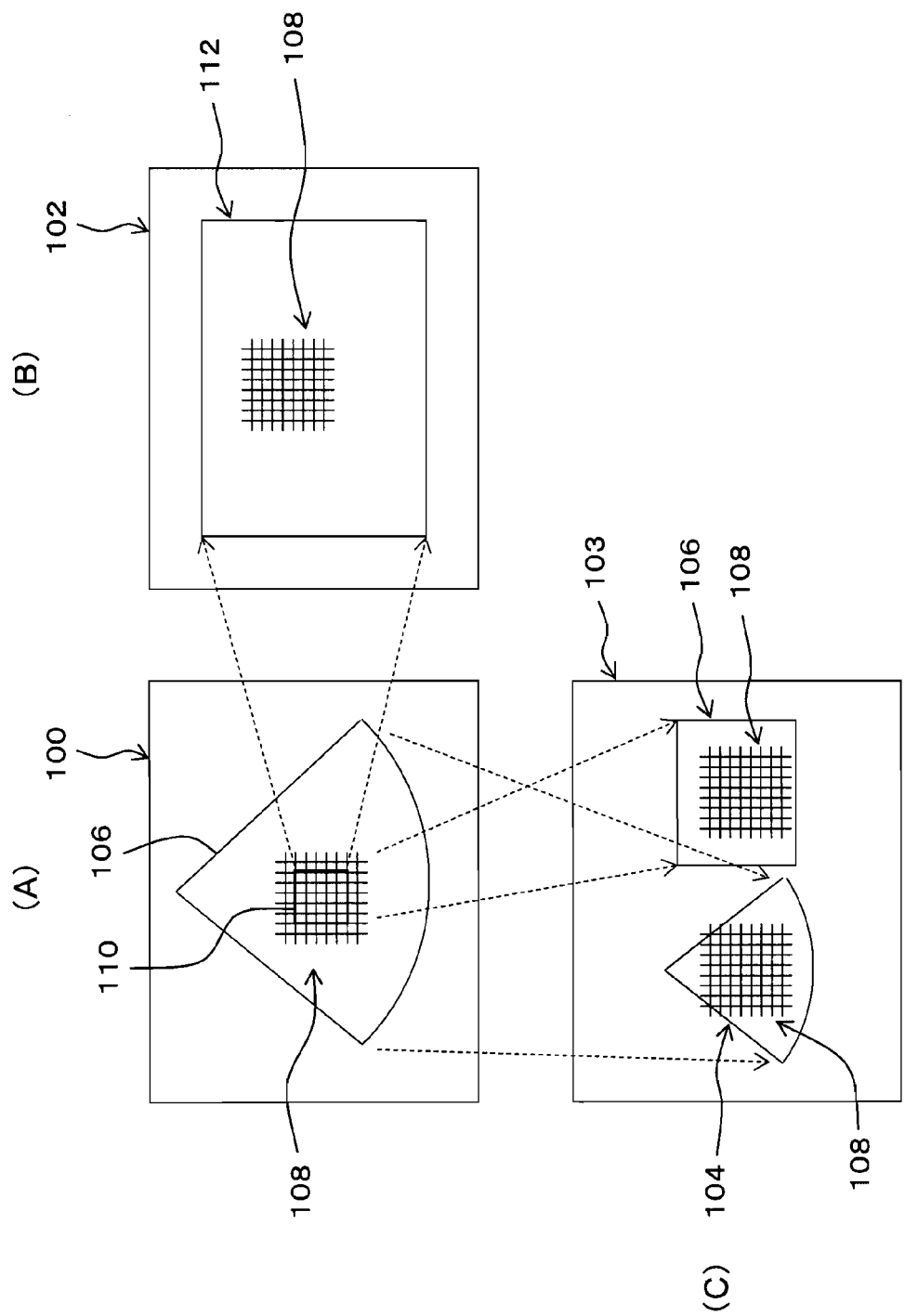
FIG. 6 View for explaining zoom processing and a plurality of conversion processes.

The operation of the scan converter module 22 illustrated in FIG. 5 will be described with reference to FIG. 6.

FIG. 6(A) illustrates a display screen 100 in which a B-mode image 106 is displayed. Here, reference numeral 108 indicates a pixel matrix in accordance with the display resolution specific to the display device in an exaggerated manner, in which, however, only a portion of the whole pixel matrix is indicated for simplification of the drawing.

In such a B-mode image 106, a region of interest (ROI) 110 is designated by the user. Here, the designation refers to specification of a zoom target. A result of the zoom processing is illustrated in FIG. 6(B). A zoomed image 112 is displayed on a display image 102. As the image is displayed on the same display device, the pixel matrix 108 in this case is the same as that illustrated in FIG. 6(A). In the present embodiment, such zoom processing is executed in the scan converter module. In other words, by operating on the content of the conversion table, the zoom processing is executed simultaneously with the scan converting processing.

FIG. 6(C) illustrates a reduced image 104 and a zoomed image 106 displayed on a display screen 103. The reduced image 104 corresponds to an image obtained by reducing the size of the B-mode image 106, and the zoomed image 106 is an enlarged image representing inside of the region of interest 110. In either image, the pixel matrix 108 is the same as that illustrated in FIG. 6(A).

In the present embodiment, by actuating the scan converting process a plurality of times based on the received frame data, these images 104 and 106 are generated substantially simultaneously. More specifically, a conversion table for generating the image 104 is used to generate the image 104, and a conversion table for generating the image 106 is used to generate the image 106. As long as the processing is completed within one display frame period, it is possible to generate any number of images. It is further possible to display these images as motion images in real time. In either case, with the use of the conversion table which is generated in consideration of the specific display resolution of the display device, the probe type, i.e. scan method, and also display conditions, it is possible to generate desired display frame data from the received frame data. Further, as, in the present embodiment, the scan converter module is substantially implemented as a function of software, it is possible to generate a plurality of images in real time by executing a single program a plurality of times to thereby execute a plurality of processes in parallel.

It is also possible to apply the similar processing to the received frame data read from the cine memory 20. As the cine memory 20 is provided upstream with respect to the scan converter module 22, i.e. as raw received frame data is stored in the cine memory 20, it is possible to process the received frame data read from the cine memory 20 as desired and display the processed data on the screen.

The invention claimed is:

1. An ultrasonic diagnostic apparatus comprising:
a scan converter module that executes conversion processing of converting received frame data obtained by transmitting and receiving ultrasound into display frame data;
a display device that is connected, via a cable, to an ultrasonic diagnostic apparatus body including the scan converter module and displays the display frame data as an ultrasonic image; and
a control unit that reads information indicating a specific display resolution from a storage unit within the display device connected to the ultrasonic diagnostic apparatus body and controls the conversion processing executed by the scan converter module based on the specific display resolution of the display device, wherein
the received frame data is formed of a plurality of beam data items in accordance with a transmitting and receiving coordinate system;
the display frame data is formed of a plurality of display line data items in accordance with a display coordinate system;
the conversion processing is processing of converting the received frame data in accordance with the transmitting and receiving coordinate system to the display frame data in accordance with the display coordinate system and the specific display resolution; and
conversion of a coordinate system and conversion of a resolution is executed simultaneously during the conversion processing in the scan converter module.

2. The ultrasonic diagnostic apparatus according to claim 1, wherein
the control unit controls the conversion processing in the scan converter module based on the specific display resolution of the display device and a display magnification of the ultrasonic image,
wherein
the conversion of a coordinate system, the conversion of a resolution, and zoom processing is executed simultaneously during the conversion processing in the scan converter module.

3. The ultrasonic diagnostic apparatus according to claim 2, wherein
the scan converter module comprises:
an address generating unit that sequentially generates a display address in accordance with the specific display resolution;
an address conversion unit that generates an address set from the display address by using an address conversion table created in accordance with the specific display resolution and the display magnification;
an interpolation unit that extracts a data set designated by the address set from the received frame data and generates interpolation data according to an interpolation operation by using the data set; and
a memory configured to construct the display frame data, the memory storing the interpolation data at a memory address corresponding to the display address.

4. The ultrasonic diagnostic apparatus according to claim 1, wherein
the control unit obtains EDID as the information indicating the specific display resolution from the display device at least one of at the time of starting up the ultrasonic diagnostic apparatus or at the time of connecting the display device to the ultrasonic diagnostic apparatus body.

5. The ultrasonic diagnostic apparatus according to claim 1, further comprising:
a receiving beam former that sequentially outputs the plurality of beam data items forming the received frame data according to phase alignment and summation processing with respect to a plurality of receiving signals obtained by transmitting and receiving the ultrasound,
wherein
each of the beam data items is formed as an echo data sequence in accordance with a diagnostic range, and
the echo data sequence output from the receiving beam former is input to the scan converter module without being subjected to re-sampling processing.

6. The ultrasonic diagnostic apparatus according to claim 2, wherein
the scan converter module converts a received frame rate corresponding to a transmitting/receiving frame rate to a predetermined display frame rate, and
the conversion of a coordinate system, the conversion of a resolution, the zoom processing, and conversion of a frame rate are executed simultaneously during the conversion processing in the scan converter module.

7. The ultrasonic diagnostic apparatus according to claim 1, wherein
the scan converter module executes n conversion processes for generating n types (where n is an integer which is 2 or greater) of display frame data from the received frame data,
each of display frame data items forming the n types of display frame data is formed of the plurality of display line data items in accordance with the display coordinate system, and
the conversion of a coordinate system and the conversion of a resolution are executed simultaneously during each of the n conversion processes.

8. The ultrasonic diagnostic apparatus according to claim 7, wherein
the scan converter module generates the n types of display frame data on a storage region within one period of the display frame rate.

* * * * *